United States Patent [19]

Steinman

[11] Patent Number: 5,409,461
[45] Date of Patent: Apr. 25, 1995

[54] CATHETER INTRODUCER ASSEMBLY WITH NEEDLE SHIELDING DEVICE

[75] Inventor: Christopher P. Steinman, Sandy, Utah

[73] Assignee: Becton Dickinson and Company, Franklin Lakes, N.J.

[21] Appl. No.: 127,722

[22] Filed: Sep. 28, 1993

[51] Int. Cl.⁶ ............................................. A61M 5/00
[52] U.S. Cl. .................................. 604/110; 604/164; 604/167; 128/917
[58] Field of Search ................... 604/53, 93, 110, 117, 604/164–168, 174, 192, 198, 256, 264, 272, 283, 177; 128/917, 169

[56] References Cited

U.S. PATENT DOCUMENTS

| | | | |
|---|---|---|---|
| Re. 34,416 | 10/1993 | Lemieux | 604/164 |
| 3,592,192 | 7/1971 | Harautuneian | 128/214.4 |
| 4,160,450 | 7/1979 | Doherty | 128/214.4 |
| 4,177,809 | 12/1979 | Moorehead | . |
| 4,676,783 | 6/1987 | Jagger et al. | 604/171 |
| 4,781,692 | 11/1988 | Jagger et al. | 604/164 |
| 4,846,805 | 7/1989 | Sitar | 604/165 |
| 4,894,052 | 1/1990 | Crawford | 604/165 |
| 4,927,415 | 5/1990 | Brodsky | 604/164 |
| 4,929,241 | 5/1990 | Kulli | 604/263 |
| 4,944,728 | 7/1990 | Carrell et al. | 604/110 |
| 4,969,876 | 11/1990 | Patterson | 604/171 |
| 5,007,901 | 4/1991 | Shields | 604/110 |
| 5,011,469 | 4/1991 | Buckberg et al. | 604/53 |
| 5,059,180 | 10/1991 | McLees | 604/110 |
| 5,137,515 | 8/1992 | Hogan | 604/110 |
| 5,163,913 | 11/1992 | Rantanen-Lee et al. | 604/177 |
| 5,215,528 | 6/1993 | Purdy et al. | 604/164 |
| 5,267,971 | 12/1993 | Brimhall | 604/177 |
| 5,267,975 | 12/1993 | Brodsky | 604/110 |
| 5,279,591 | 1/1994 | Simon | 604/263 |
| 5,304,144 | 4/1994 | Brimhall | 604/177 |
| 5,306,253 | 4/1994 | Brimhall | 604/165 |

FOREIGN PATENT DOCUMENTS 0314470  5/1989  European Pat. Off. ............. 604/53

*Primary Examiner*—C. Fred Rosenbaum
*Assistant Examiner*—Mark Bockelman
*Attorney, Agent, or Firm*—Michael G. Schwarz; Eric M. Lee

[57] ABSTRACT

A winged catheter introducer is disclosed. The catheter introducer has a catheter, a robe attached to the catheter and a winged intermediate member between the catheter and the robe. Within the catheter and the robe is a needle with a stylet attached to it. The stylet is attached to a hub which facilitates the pulling of the needle out of the catheter and through the robe. Attached to the robe is an adapter with a septum attached to it. The needle is provided with an opening extending from the needle wall to the needle lumen. A shielding device is provided which is attached to the adapter. The shielding device includes a needle container which is designed to trap the needle. A needle shield is provided inside the needle container. The needle is provided with an area of enlarged diameter. This area of enlarged diameter interacts with the needle shield when the needle is withdrawn from the catheter and robe and into the needle container. The needle shield is provided with an orifice through which the needle and stylet can fit but through which the area of enlarged diameter cannot pass. When the needle is withdrawn from the catheter and tube and into the needle container, it is trapped by the needle shield. The needle shield is also provided with a transverse wall which snaps over the point of the needle.

5 Claims, 6 Drawing Sheets

CATHETER INTRODUCER ASSEMBLY WITH NEEDLE SHIELDING DEVICE

BACKGROUND

This invention relates generally to catheter introducer devices. In particular, it relates to a catheter introducer having an introducer needle and a device for shielding the needle after use.

Catheter introducers for introducing catheters into the blood vessels of patients are well known. Such devices typically comprise a sharp introducer needle and a catheter tube for insertion into a blood vessel. The needle is used to assist in piercing the skin and the blood vessel and introducing the catheter tube into the blood vessel. When such a procedure is performed, the needle may become contaminated with blood. The advent of AIDS has resulted in an increased awareness of the risks associated with blood borne pathogens such as AIDS and hepatitis. There is therefore a need for devices to shield catheter introducer needles to lower the risk of healthcare workers and members of the public being infected by used catheter introducer needles.

SUMMARY OF THE INVENTION

The present invention is a type of catheter introducer set based on a conventional Intima TM or Angioset ® type available from Becton Dickinson and Company of Franklin Lakes, N.J. The device has a catheter for insertion into a body. The catheter has a proximal end, a distal end and a first lumen. Located axially inside the catheter lumen is a needle having a proximal end and a sharp distal end. The needle is disposed axially within the first lumen such that the sharp distal end of the needle protrudes from the distal end of the catheter. A tube having a proximal end, a distal end and a second lumen is connected to the proximal end of the catheter. The second lumen is dimensioned to accommodate at least part of the needle axially. Attached to the proximal end of the tube is a needle container having a proximal end and a distal end and a passage between the two ends for accommodating the needle. The needle container has a proximal orifice at the proximal end and a distal orifice at the distal end. The distal end of the needle container is connected to the proximal end of the adapter.

Located substantially in the needle container is a needle shield having a first engagement means for engaging the needle. The first engagement means prevents the needle from exiting the needle container through the proximal orifice. The needle shield also has a transverse wall for blocking the distal orifice on passage of the sharp distal tip of the needle into the needle container. This prevents the needle from exiting the needle container through the distal orifice.

DETAILED DESCRIPTION

In the following detailed description of the preferred embodiment, reference is made to the accompanying drawings which form a part hereof, and in which is shown by way of illustration a specific embodiment in which the invention may be practiced. This embodiment is described in sufficient detail to enable those skilled in the art to practice the invention, and it is to be understood that other embodiments may be utilized and that structural changes may be made without departing from the scope of the present invention. The following detailed description is, therefore, not to be taken in a limiting sense, and the scope of the present invention is defined by the appended claims.

Figure 1:
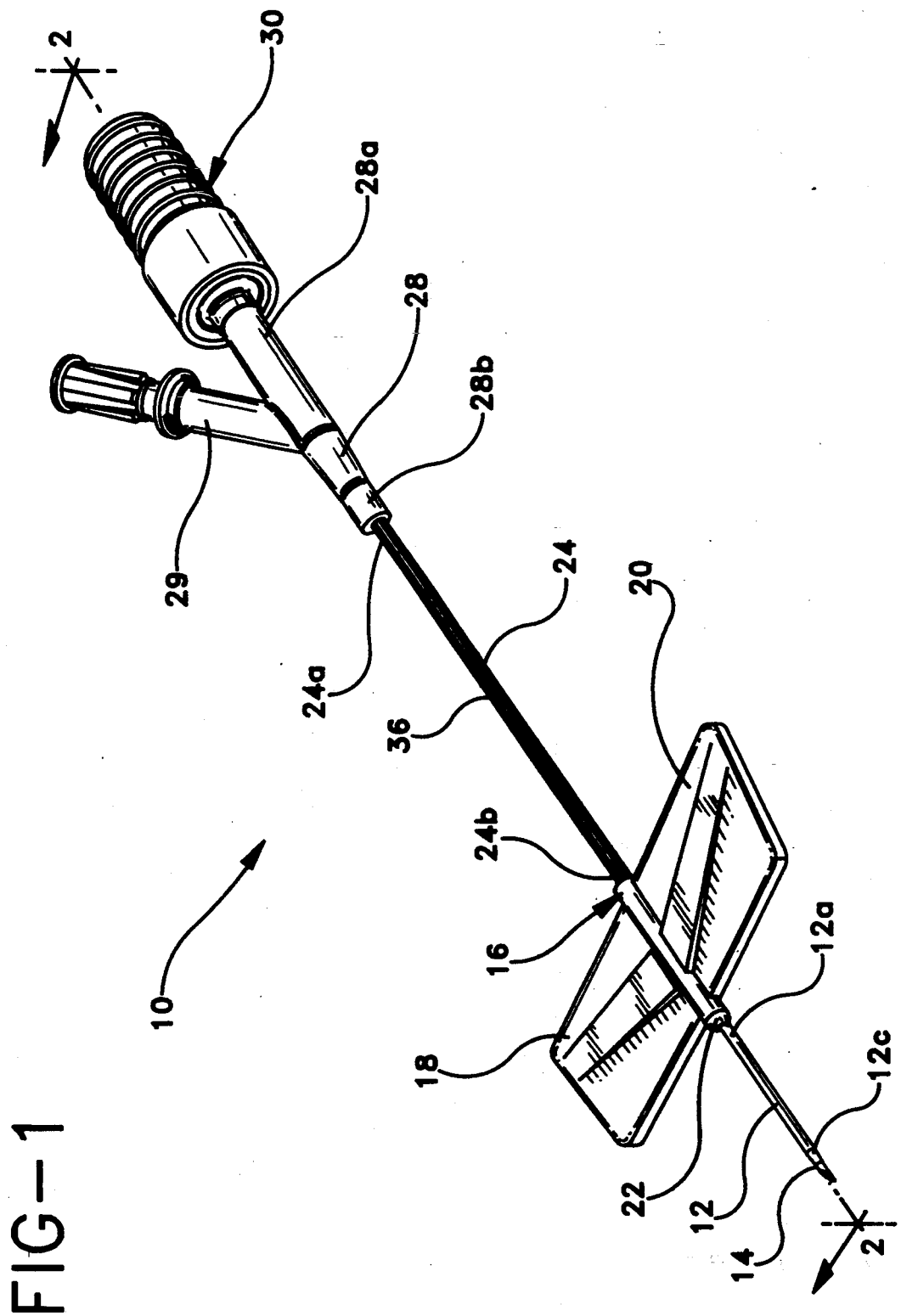
FIG. 1 is a perspective view of the invention.

Catheter introducer 10 is shown in FIG. 1. Catheter introducer 10 is of a type sold by Becton Dickinson and Company of Franklin Lakes, N.J. under the names Intima TM and Angioset ® and described in U.S. Pat. Nos. 5,163,913 and 4,177,809 which are incorporated by reference. The device has an over the needle catheter 12 for insertion into a blood vessel or any part of the body so that fluids can be infused into or withdrawn from the body. Catheter 12 has proximal end 12a, distal end 12b and lumen 12c. Catheter 12 fits concentrically over needle 14 which has proximal end 14a and sharp distal end 14b. Catheter 12 is connected to intermediate member 16 which has wings 18 and 20 and hub 22, to which catheter 12 is attached in manner described in U.S. Pat. No. 5,163,913. Wings 18 and 20 are used in the insertion of catheter 16 into the body in a manner well known of those of skill in the art.

Figure 2:
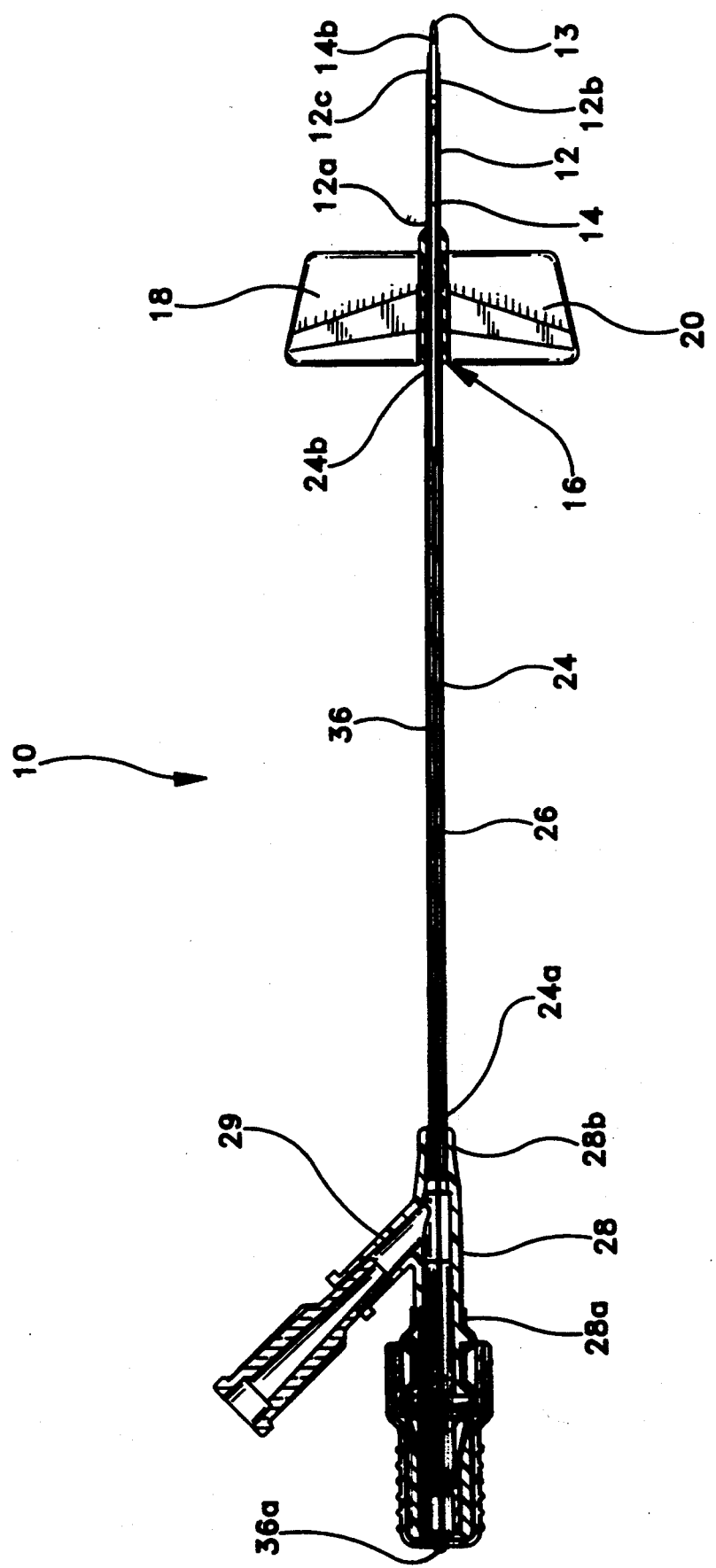
FIG. 2 is a cross sectional top view of the invention.

Attached to intermediate member 16 is tube 24, a polyvinylchloride tube having proximal end 24a, distal end 24b and lumen 24c. Distal end 24b is thus connected to catheter 12 via intermediate member 16. Tube 24 has an internal lumen 26 (see FIG. 2) which is dimensioned to accommodate at least part of the needle 14 axially.

Connected to proximal end 24a of tube 24 is adapter 28 which has proximal end 28a and distal end 28b. Distal end 28b is connected to proximal end 24a of tube 24. Adapter 28 has a Y-port 29 integrally molded into it.

Figure 3:
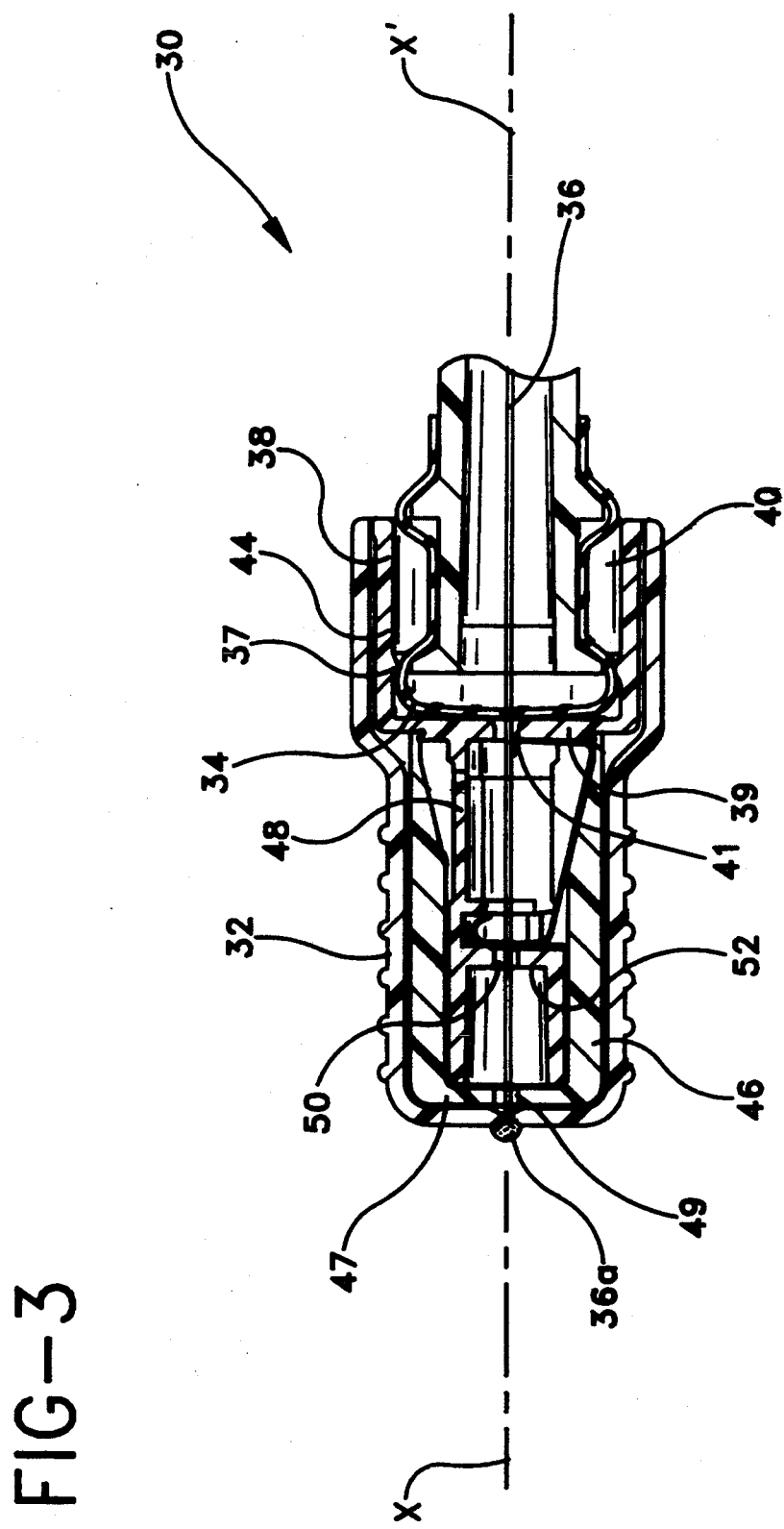
FIG. 3 is a close up cross sectional view of the needle container of the invention prior to activation of the needle shield.

FIG. 3 shows adapter 28 and needle container 30 in greater detail. Attached to proximal end 28a of adapter 28 is septum 34, known to those of ordinary skill in the art as a "PRN" from the Latin "pro re nata" meaning "as the need arises". Septum 34 will be referred to as a PRN 34. PRN 34 is made of rubber. It permits the insertion of a sharp hypodermic needle in order to infuse or withdraw fluids through catheter 12. On withdrawal of the needle, PRN 34 reseals itself. PRN may be pre-slit to facilitate the insertion of a blunt cannula rather than a sharp needle.

Connected to proximal end 28a of adapter 28 at PRN 34 is needle container 30 (see FIG. 3). Needle container 30 has proximal end 30a and distal end 30b. Distal end 30b is connected to proximal end 28a of adapter 28.

Needle 14 is attached to distal end 36b of stylet 36 in a manner as described in U.S. Pat. No. 4,177,809. Both needle 14 and stylet 36 can be withdrawn axially through PRN 34. Stylet 36 is provided with hub 32 which facilitates the pulling of needle 14 axially through catheter 12, tube 24, adapter 28 and into needle container 30. Hub 32 is secured to the proximal end 36a of stylet by means of a drop of epoxy resin.

Figure 4:
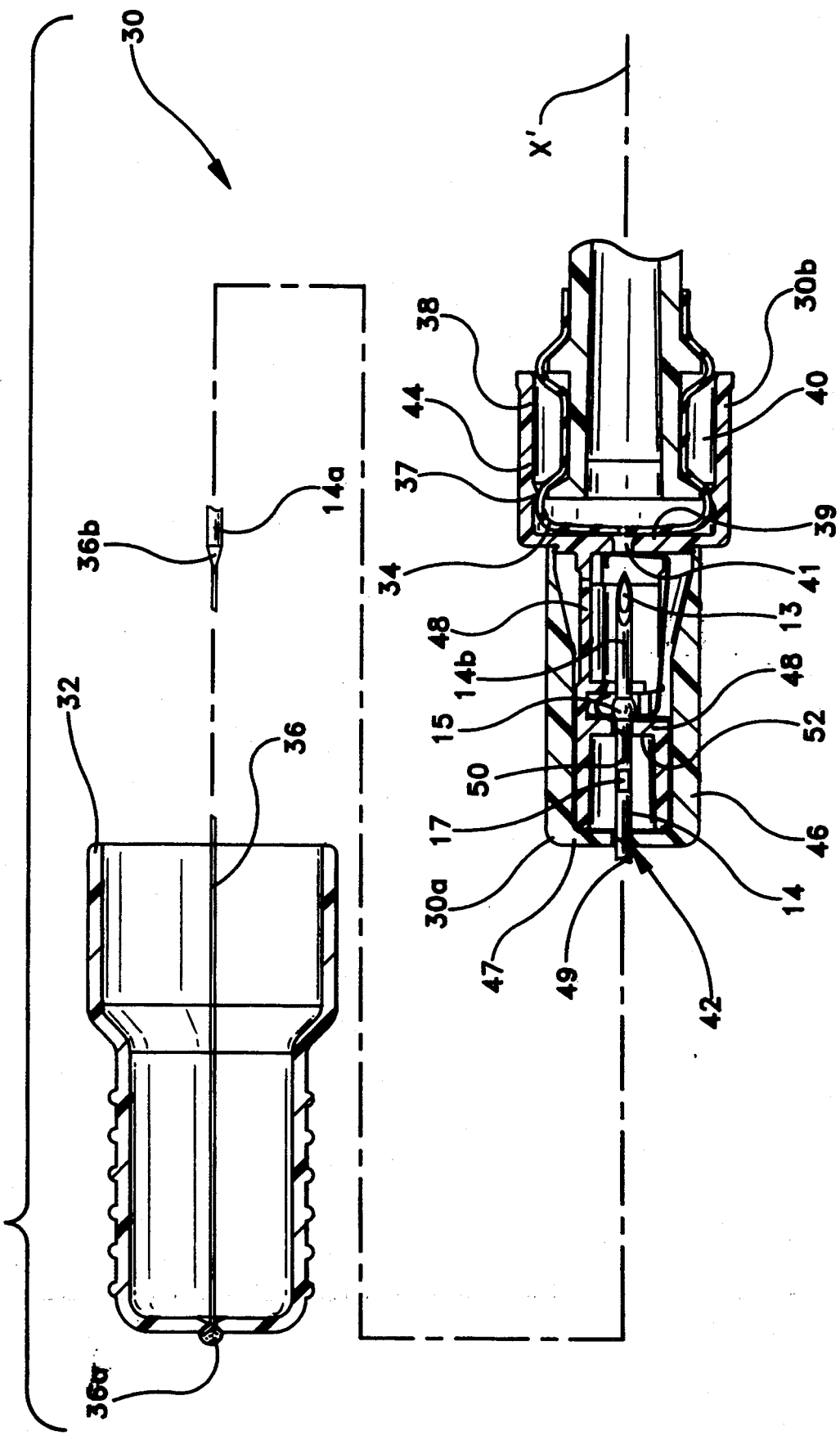
FIG. 4 is a close up cross sectional view of the needle container of the invention with the needle shield activated.
Figure 5:
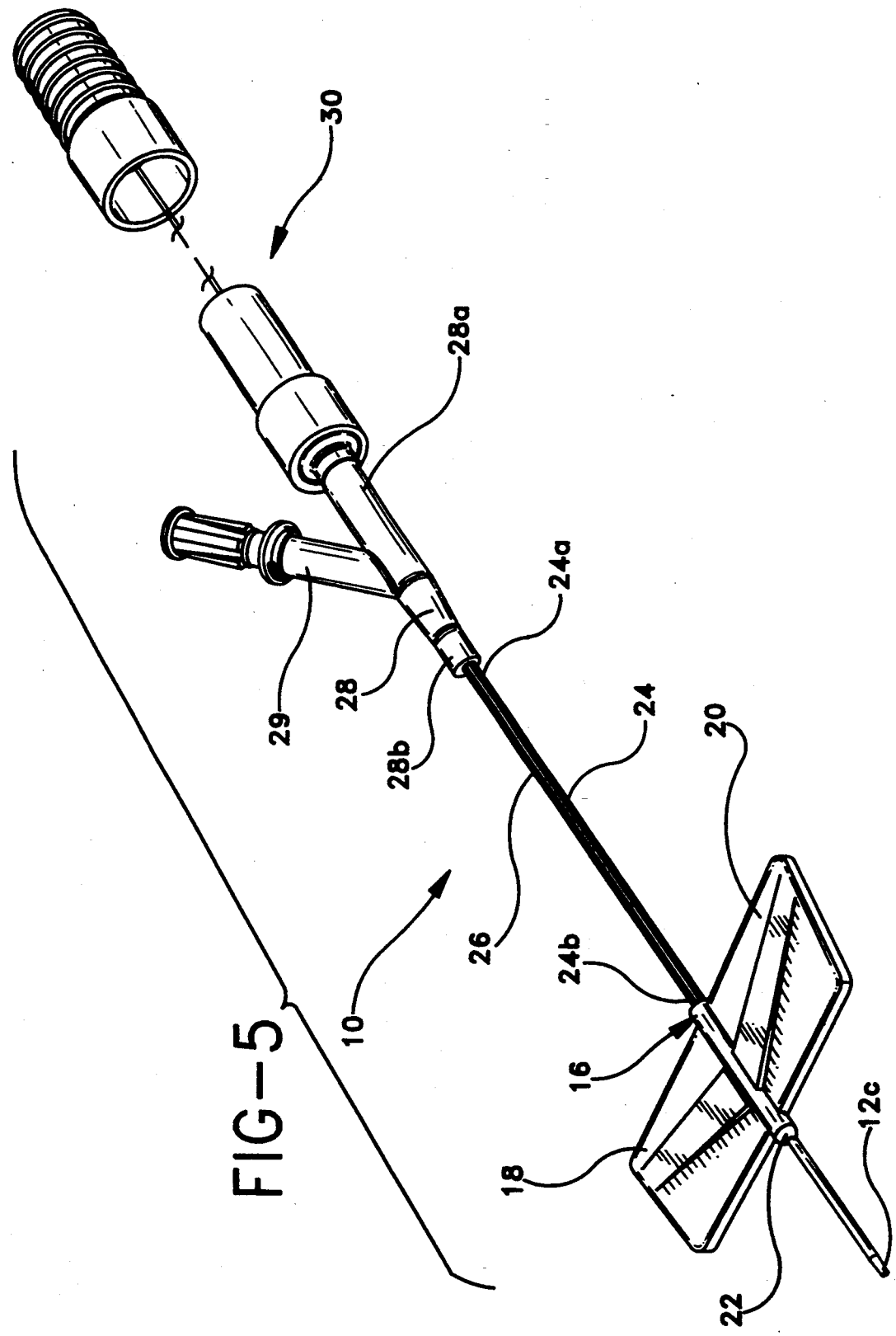
FIG. 5 is a perspective view of the invention with the needle shielded.

Needle 14 is provided with an area of enlarged diameter, collar 15, near distal end 14b (see FIG. 4). This area 14 is formed on the needle by a centerless grinding or cold forming process. Needle 14 is also provided with a side opening 17 which permits fluid flow out of lumen 13 of needle 14. This opening permits the observation through catheter 12 of blood flashback as needle 14 enters a blood vessel, thereby assisting in introducing catheter 12 into the vessel. This feature is described in U.S. Pat. No. 4,894,052 which is incorporated herein by reference.

Catheter 12 is introduced into the body in a manner well known in the art. Once catheter 12 has been inserted, needle 14 is withdrawn by pulling on hub 32 so that needle 14 emerges, proximal end first, from PRN 34.

Needle container 30 is made up of two co-axial generally cylindrical members 44 and 46. Member 44 comprises annular rim 38 and rear wall 39. Rear wall 39 is provided with orifice 41 dimensioned to permit the passage of needle 14 axially therethrough. Member 46 has a rear wall 47 provided with orifice 49 which supports needle 14 as it passes into needle container 30. Within member 46 is snugly disposed support 48. Support 48 has a rear wall 52 provided with second orifice 50. Orifice 50 is dimensioned to allow needle 14 to pass through it axially until it strikes collar 15 which prevents further passage of needle 14. A rubber plug 42 may be placed in orifice 49 to keep blood from passing in or out of member 46. Plug 42 also wipes needle 14 and stylet 36 as they pass through orifice 49, thus reducing the amount of blood on needle 14 and stylet 36.

At distal end 30b of needle container 30 is annular rim 38 defining cavity 40 which enables needle container 30 to snap fit onto PRN 34. Annular rim is provided with an inner annular collar 37 for facilitating a snap fit onto PRN 34. PRN 34 fits snugly into cavity 40 such that the axes of tube 24 and needle container 30 are substantially co-axial as shown in FIG. 4. When needle container 30 is attached to PRN 34 as shown in FIG. 3, the axes of needle 14 and stylet 36 align with axis X—X' and needle 14 can thus be drawn axially into needle container 30 by pulling hub 32.

Figure 6:
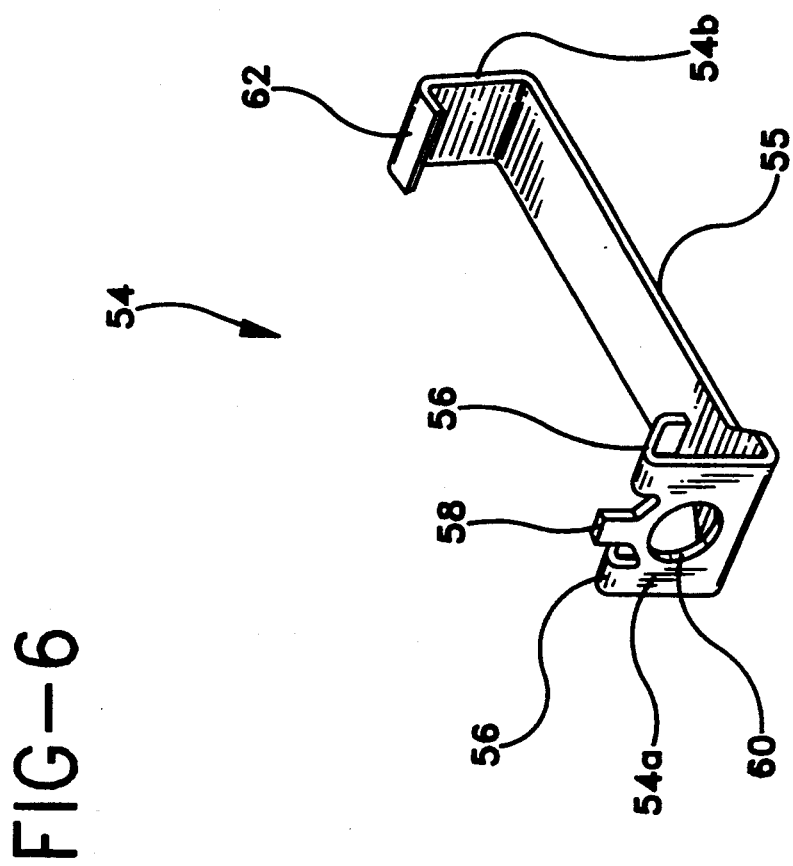
FIG. 6 is a close up perspective view of the needle shield of the invention.

Held by support 48 is needle shield 54 shown in detail in FIG. 6. Needle shield 54 has proximal end 54a, distal end 54b and an intermediate portion 55. Proximal and distal ends 54a and 54b are bent substantially at 90° to intermediate portion 55. Distal end 54b forms transverse wall, the purpose of which will become apparent. Distal end 54b also has a flange 62 which is substantially parallel to intermediate portion 55. Proximal end 54a has two similar flanges 56 and a projection 58 which assist in the location of needle shield in support 48. Distal end 54b is also provided with an orifice 60 which is dimensioned to allow needle 14 and stylet 36 to pass through it until collar 15 of needle 14 reaches it. Needle shield 54 is made of a resilient material such as steel and is biased so that distal end 54b tends in a direction transverse to axis X—X' (see FIGS. 3 and 4). Distal end 54b can snap over distal tip 14b of needle 14 when needle 14 enters container 30.

Prior to activation of needle shield 54, due to the bias of needle shield 54, needle shield 54 abuts stylet 36 as shown in FIG. 3. Once catheter 12 has been introduced into a vessel, needle 14 is withdrawn by pulling on hub 32. Needle 14 thus moves axially through lumen 24c to needle container 30, entering member 46 through first orifice 41. When needle tip 14b passes through first orifice 41 and into member 46, distal end 54b of needle shield 54 snaps over needle tip 14b as shown in FIG. 4 due to the bias of needle shield 54. Needle collar 15 then reaches proximal end 54a of needle shield 54. Due to the relative dimensions of collar 15 and orifice 60, needle 14 is prevented from further movement in the proximal direction. Needle tip 14 is thus prevented from exiting member 46 in the distal direction by distal end 54b of needle shield 54 and is prevented from exiting in the proximal direction by proximal end 54a.

Needle container 30 can be removed from PRN 34 by pulling hub 32 in a proximal direction. PRN 34, adapter 28, tube 24, intermediate member 16 and catheter 12 remain with the patient. Needle tip 14b is confined in needle container 30. Hub 32, stylet 36, needle 14 and needle container 30 can be safely disposed of.

I claim:

1. A catheter introducer assembly, comprising:
    a catheter having a proximal end and a distal end;
    an adaptor in fluid communication with the catheter;
    a needle defining a needle lumen and having a sharp distal tip and a proximal end, the needle being initially disposed coaxially within the catheter such that the sharp distal tip extends beyond the distal end of the catheter and wherein the needle has a region of enlarged diameter adjacent to the sharp distal tip and wherein the needle further defines a side opening adjacent to and proximal to the region of enlarged diameter;
    a stylet having a proximal end and a distal end connected to the proximal end of the needle;
    a hub connected to the proximal end of the stylet;
    a needle container removably connected to the adaptor, the needle container defining a distal opening through which the stylet and the needle may extend and which is sized to allow the region of enlarged diameter on the needle to pass therethrough and a proximal opening proximal of the distal opening and through which the stylet and the needle may extend and which is sized to create an interference fit with the needle;
    a support disposed in the needle container, the support defining an intermediate opening proximal of the distal opening and through which the stylet and the needle may extend but which is sized so as not to allow the region of enlarged diameter on the needle to pass therethrough; and
    a needle shield associated with the needle container, the needle shield having a transverse wall that covers the distal opening in the needle container when the sharp distal tip of the needle is moved proximally into the needle container; and
    wherein the side opening is located in the needle container when the sharp distal tip of the needle is in the needle container and the region of enlarged diameter on the needle is adjacent to the support.

2. The catheter introducer assembly of claim 1 wherein the hub initially substantially surrounds the needle container.

3. The catheter introducer assembly of claim 1 further comprising a septum secured to the proximal end of the adaptor.

4. The catheter introducer assembly of claim 3 wherein the hub initially substantially surrounds the needle container.

5. The catheter introducer assembly of claim 4 wherein the stylet is connected to the needle to close the needle lumen and prevent fluid flow through the proximal end of the needle.

* * * * *

UNITED STATES PATENT AND TRADEMARK OFFICE
CERTIFICATE OF CORRECTION

PATENT NO.  : 5,409,461
DATED       : April 25, 1995
INVENTOR(S) : Christopher P. Steinman It is certified that error appears in the above-identified patent and that said Letters Patent is hereby corrected as shown below:

In the Abstract

```
Line 2, change "robe" to --tube--;
Line 4, change "robe", both occurrences, to --tube--;
Line 7, change "robe" to --tube--;
Line 8, change "robe" to --tube--; and
Line 17, change "robe" to --tube--.
```

Signed and Sealed this

Twenty-ninth Day of August, 1995

Attest:

BRUCE LEHMAN

*Attesting Officer*          *Commissioner of Patents and Trademarks*